(12) United States Patent
Yoshioka et al.

(10) Patent No.: US 6,558,346 B1
(45) Date of Patent: May 6, 2003

(54) AUTOMATIC CONTROL-TYPE, PORTABLE INTRAVENOUS INFUSION APPARATUS AND JACKET THEREFOR

(75) Inventors: Wataru Yoshioka, Hyogo-ken (JP); Ryosuke Homma, Osaka (JP)

(73) Assignee: Medico's Hirata Inc., Osaka (JP)

( * ) Notice: Subject to any disclaimer, the term of this patent is extended or adjusted under 35 U.S.C. 154(b) by 0 days.

(21) Appl. No.: 09/504,582

(22) Filed: Feb. 15, 2000

(30) Foreign Application Priority Data

May 10, 1999 (JP) .......................................... 11-129251

(51) Int. Cl.$^7$ ................................................ A61M 5/00
(52) U.S. Cl. ...................... 604/67; 604/70; 604/118; 604/141; 604/246; 604/253
(58) Field of Search .............................. 604/65, 67, 70, 604/118, 122, 131–133, 140–142, 151, 246, 247, 250, 253, 260, 262

(56) References Cited

U.S. PATENT DOCUMENTS

| | | | |
|---|---|---|---|
| 4,684,367 A | * 8/1987 | Schaffer et al. | 604/140 |
| 4,735,613 A | * 4/1988 | Bellin et al. | 604/141 |
| 4,890,984 A | 1/1990 | Alderson et al. | |
| 5,399,166 A | 3/1995 | Laing | |
| 5,584,811 A | 12/1996 | Ross et al. | |
| 6,159,186 A | * 12/2000 | Wickham et al. | 604/251 |
| 6,280,408 B1 | * 8/2001 | Sipin | 604/65 |

FOREIGN PATENT DOCUMENTS

WO     95-00191     1/1995

* cited by examiner

*Primary Examiner*—J. Casimer Jacyna
(74) *Attorney, Agent, or Firm*—Browdy and Neimark, P.L.L.C.

(57) ABSTRACT

The automatic control-type, portable intravenous infusion apparatus includes an infusion liquid container to which an infusion liquid tube is connected, pressurize it, the infusion liquid tube being provided with a drip-monitoring tube, a connector and an infusion needle with a pressurizing bag for holding the infusion liquid container. The infusion liquid container includes an inflatable pressurizing bag and a sheet member having side ends each fixed to the side ends of the pressurizing bag. Connected to the pressurizing bag are an air tube provided with a mechanical safety valve, a selector valve and an air pump. By introducing air into the infusion liquid container, the pressurizing bag is inflated to apply substantially a constant pressure to the infusion liquid container, thereby flowing the infusion liquid from the container and keeping the dropping speed there substantially constant.

6 Claims, 12 Drawing Sheets

AUTOMATIC CONTROL-TYPE, PORTABLE INTRAVENOUS INFUSION APPARATUS AND JACKET THEREFOR

BACKGROUND OF THE INVENTION

The present invention relates to a portable intravenous infusion apparatus that can be taken out of a hanger and carried by a patient when the patient leaves the bed, particularly to an automatic control-type, portable intravenous infusion apparatus capable of keeping the amount of an infusion liquid substantially at a constant level safely and surely, and a jacket for carrying such a portable intravenous infusion apparatus.

A conventional infusion liquid container is suspended from a hanger to infuse a liquid in the bag into a patient by the action of gravity. When the patient leaves the bed, the patient should move with the infusion liquid container suspended from the hanger. Accordingly, the freedom of patient's body is restricted, causing the hospitalized patient's life painful.

Under such circumstances, proposal has been made to provide, as an instillator that can be carried by a patient freely, a portable intravenous infusion apparatus comprising a pressurizing bag having a sheet member fixed thereto along both side ends; a manual air pump for supplying a pressurizing air to the pressurizing bag; and an infusion liquid container disposed between the pressurizing bag and the sheet member, the pressurizing bag being inflated to press the infusion liquid container, thereby causing the infusion liquid to drop from a tube connected to the bag, and such portable intravenous infusion apparatus is commercially sold. However, because the pressurizing air is manually supplied, the handling of this portable intravenous infusion apparatus is troublesome with pressure in the pressurizing bag largely variable, and it is difficult to keep the dropping speed of the infusion liquid constant.

OBJECT AND SUMMARY OF THE INVENTION

Accordingly, an object of the present invention is to provide a portable intravenous infusion apparatus that can be taken out of a hanger and carried by a patient when the patient leaves the bed.

Another object of the present invention is to provide an automatic control-type, portable intravenous infusion apparatus capable of being carried by a patient freely and providing a substantially constant dropping speed of an infusion liquid safely and surely.

A further object of the present invention is to provide a jacket that a patient can wear to carry such a portable intravenous infusion apparatus.

As a result of intense research in view of the above objects, the inventors have found that by providing an infusion liquid container with a means for applying a substantially constant pressure to an infusion liquid in the container, the infusion liquid can be infused substantially at a constant speed to the patient without necessitating it to use the action of gravity by hanging, and that by providing a pressurizing bag for holding an infusion liquid container with an air pump for automatically supplying a pressurizing air to the pressurizing bag, and by controlling a supply speed of the pressurizing air and/or the dropping speed of the infusion liquid based on the air pressure in the pressurizing bag and/or the dropping speed of the infusion liquid, it is possible to automatically control the dropping speed of the infusion liquid substantially constant safely and surely. The inventors have also found that a patient can easily carry such a portable intravenous infusion apparatus with a jacket having pockets for receiving an infusion liquid container and a pressure-applying means. The present invention has been completed based on these findings.

Thus, the portable intravenous infusion apparatus according to the present invention comprises an infusion liquid container; an infusion liquid tube communicating with the infusion liquid container; an infusion needle mounted to a tip end of the infusion liquid tube; and a means for applying a substantially constant pressure to the infusion liquid container.

The pressure-applying means preferably comprises (a) a pressurizing bag inflatable by charging air; (b) a sheet member having each side end fixed to each side end of the pressurizing bag, a width of the sheet member being slightly larger than a lateral width of the pressurizing bag in a deflated state; (c) an air tube communicating with the pressurizing bag; (d) an air-supplying means mounted to the air tube; (e) and a safety valve mounted to the air tube, wherein the infusion liquid container is disposed in a space between the pressurizing bag and the sheet member, and wherein the pressurizing bag is inflated by the introduction of air by the air-supplying means, whereby a substantially constant pressure is applied to the infusion liquid container to cause an infusion liquid to flow therefrom.

In another preferred embodiment of the present invention, the pressure-applying means comprises (a) an annular pressurizing bag comprising a plurality of air chambers inflatable inwardly by charging air; (b) an air tube communicating with the annular pressurizing bag; and (c) an air-supplying means mounted to the air tube, wherein the infusion liquid container is disposed in a space defined by an inner wall of the annular pressurizing bag, and wherein the pressurizing bag is inflated inwardly by the introduction of air by the air-supplying means, whereby a substantially constant pressure is applied to the infusion liquid container to cause an infusion liquid to flow therefrom.

In a further preferred embodiment of the present invention, the pressure-applying means comprises (a) an inflatable balloon disposed inside the infusion liquid container; (b) an air tube communicating with the balloon; and (c) an air-supplying means mounted to the air tube, wherein the balloon is inflated by the introduction of air by the air-supplying means, whereby a substantially constant pressure is applied to the infusion liquid container to cause an infusion liquid to flow therefrom.

In a still further preferred embodiment of the present invention, the pressure-applying means comprises (a) an infusion needle disposed inside the infusion liquid container; (b) an air tube communicating with the infusion needle; and (c) an air-supplying means mounted to the air tube, wherein air is introduced into the infusion liquid container through the infusion needle by the air-supplying means, whereby a substantially constant pressure is applied to the infusion liquid container to cause an infusion liquid to flow therefrom.

The first automatic control-type, portable intravenous infusion apparatus according to the present invention comprises (a) a pressurizing bag means for holding an infusion liquid container to pressurize the infusion liquid container to cause an infusion liquid to flow therefrom; (b) an air pump for supplying a pressurizing air to the pressurizing bag means; (c) a pressure sensor for detecting pressure in the pressurizing bag means; and (d) a control means for controlling the amount of air supplied from the air pump to the pressurizing bag means depending on an output of the pressure sensor, wherein the pressure in the pressurizing bag means is compared with a reference pressure by the control means, and wherein the air pump is operated when the pressure in the pressurizing bag means is lower than the reference pressure, thereby increasing the pressure of the pressurizing bag means to keep the dropping speed of the infusion liquid substantially constant.

The second automatic control-type, portable intravenous infusion apparatus according to the present invention comprises (a) a pressurizing bag means for holding an infusion liquid container to pressurize the infusion liquid container to cause an infusion liquid to flow therefrom; (b) an air pump for supplying a pressurizing air to the pressurizing bag means; (c) a drop counter mounted to a drip-monitoring tube for counting the dropping of the infusion liquid; and (d) a control means for controlling the amount of air supplied from the air pump to the pressurizing bag means depending on an output of the drop counter, wherein the count number of infusion liquid drops measured by the drop counter is compared with a reference drop count number by the control means, and wherein the air pump is operated when the measured drop count number is smaller than the reference drop count number, thereby increasing the pressure of the pressurizing bag means to keep the dropping speed of the infusion liquid substantially constant.

The third automatic control-type, portable intravenous infusion apparatus according to the present invention comprises (a) a pressurizing bag means for holding an infusion liquid container to pressurize the infusion liquid container to cause an infusion liquid to flow therefrom; (b) an air pump for supplying a pressurizing air to the pressurizing bag means; (c) a drop counter mounted to a drip-monitoring tube for counting the dropping of the infusion liquid; (d) a clamp device mounted to the infusion liquid tube for controlling the amount of the infusion liquid flowing through the infusion liquid tube; and (e) a control means for controlling the clamp device depending on an output of the drop counter, wherein the count number of infusion liquid drops measured by the drop counter is compared with a reference drop count number by the control means, and wherein the clamp device is operated to decrease or increase the dropping speed of the infusion liquid when the measured drop count number is larger or smaller than the reference drop count number, thereby controlling the dropping speed of the infusion liquid substantially constant.

The automatic control-type, portable intravenous infusion apparatus according to a preferred embodiment of the present invention comprises (a) a pressurizing bag means for holding an infusion liquid container to pressurize the infusion liquid container to cause an infusion liquid to flow therefrom; (b) an air pump for supplying a pressurizing air to the pressurizing bag means; (c) a pressure sensor for detecting pressure in the pressurizing bag means; (d) a drop counter mounted to a drip-monitoring tube for counting the dropping of the infusion liquid; (e) a clamp device mounted to the infusion liquid tube for controlling the amount of the infusion liquid flowing through the infusion liquid tube; and (f) a control means receiving an output of the pressure sensor and/or an output of the drop counter to generate a signal for controlling the air pump and/or the clamp device, wherein the comparison of the measured pressure of the pressurizing bag means with a reference pressure and the comparison of the measured drop count number with the reference drop count number are carried out by the control means, wherein the air pump is operated and/or the clamp device is operated to open the infusion liquid tube when the measured pressure of the pressurizing bag means is lower than the reference pressure, and/or when the measured drop count number is smaller than the reference drop count number, and wherein the air pump is stopped and/or the clamp device is operated to clamp the infusion liquid tube when the measured pressure of the pressurizing bag means is higher than the reference pressure, and/or when the measured drop count number is larger than the reference drop count number, thereby keeping the dropping speed of the infusion liquid substantially constant.

In another preferred embodiment of the present invention, the infusion liquid tube is further provided with a bubble sensor, and the air tube is further provided with a safety valve, both of the bubble sensor and the safety valve being connected to the control means, whereby the safety valve is opened when the bubble sensor detects a bubble in the infusion liquid flowing through the infusion liquid tube.

In a further preferred embodiment of the present invention, the infusion liquid tube is further provided with a bubble sensor and a clamp device both connected to the control means, whereby the clamp device clamps the infusion liquid tube when the bubble sensor detects a bubble in the infusion liquid flowing through the infusion liquid tube.

In a still further preferred embodiment of the present invention, the infusion liquid tube is further provided with a bubble sensor and a clamp device, and the air tube is further provided with a safety valve, all of the bubble sensor, the clamp device and the safety valve being connected to a control means, whereby the safety valve is opened, and the clamp device is operated to clamp the infusion liquid tube, when the bubble sensor detects a bubble in the infusion liquid flowing through the infusion liquid tube.

In a still further preferred embodiment of the present invention, when pressure abnormally increases in the pressurizing bag means, the air pump is stopped, the safety valve is opened, and a buzzer and/or a lamp alarms the irregularity of pressure in the pressurizing bag means.

In a still further preferred embodiment of the present invention, the pressurizing bag means comprises a pressurizing bag and a sheet member having both side ends fixed to the pressurizing bag, and the infusion liquid container is disposed in a space between the pressurizing bag and the sheet member, the pressurizing bag being provided with a mechanical safety valve for releasing pressure when the pressure of the pressurizing bag exceeds a predetermined level.

The jacket for holding the (automatic control-type) portable intravenous infusion apparatus according to the present invention has a front-open structure comprising a pair of front parts, each of the front parts having a pocket for receiving the pressurizing bag means and the infusion liquid container, a pocket for receiving the pressure-applying means connected to the pressurizing bag means, and a horizontally extending pocket for supporting an arm to which the infusion needle is stuck, and each of the front parts further having a hook at shoulder for suspending the infusion liquid container.

DETAILED DESCRIPTION OF THE PREFERRED EMBODIMENTS

[1] Structure of Portable Intravenous Infusion Apparatus

Figure 1:
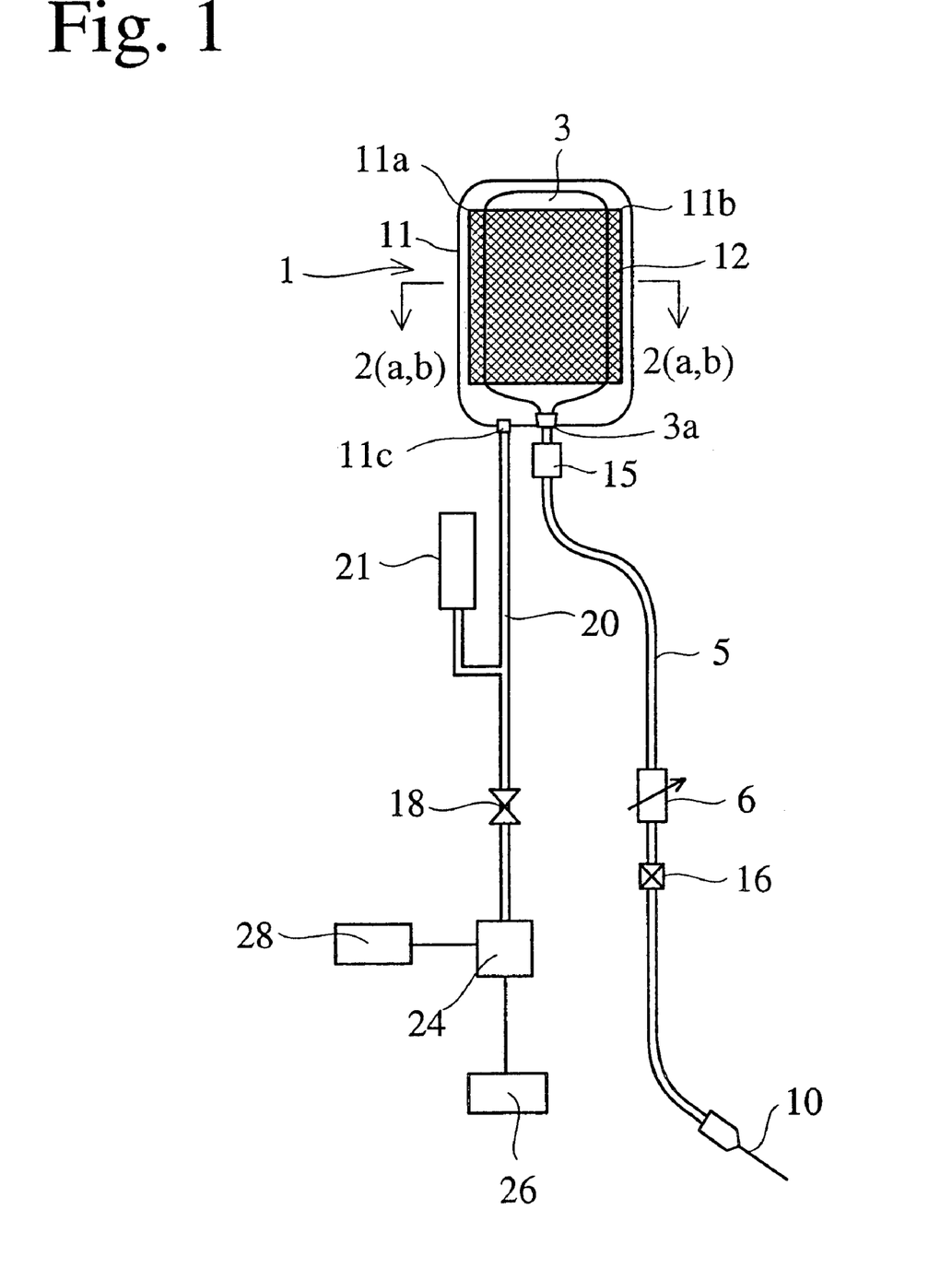
FIG. 1 is schematic view showing the overall structure of the portable intravenous infusion apparatus of the present invention.

FIG. 1 shows the overall structure of a portable intravenous infusion apparatus according to a preferred embodiment of the present invention. An infusion liquid container 3, which may be in the form of a soft plastic bag or a relatively soft plastic bottle, has a plug 3a at its bottom, to which an infusion liquid tube 5 is connected. The infusion liquid tube 5 is provided with an air vent means 15, a drip-monitoring tube 6 for monitoring the dropping of an infusion liquid, a connector 16 and an infusion needle 10 in this order from above. A pressurizing bag means 1 for holding the infusion liquid container 3 comprises an inflatable pressurizing bag 11, and a sheet member 12 having side ends each fixed to each of the side ends 11a, 11b of the pressurizing bag 11. Connected to the pressurizing bag 11 is an air tube 20 provided with a mechanical safety valve 21, a selector valve 18 and an air pump 24.

Figure 2:
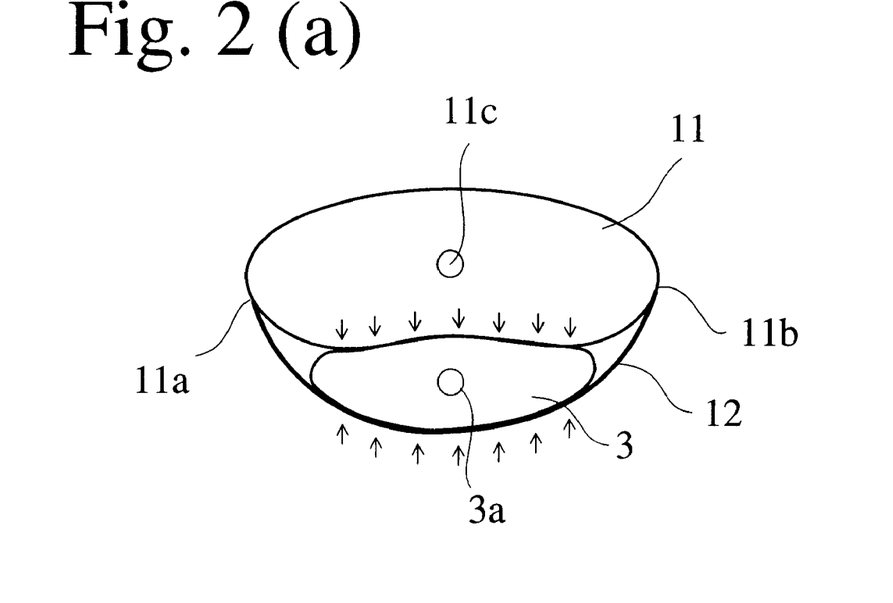
FIG. 2(a) is a cross-sectional view taken along the line A—A in FIG. 1, showing a state in which an infusion liquid container is pressed between an inflated pressurizing bag and a sheet member.
FIG. 2(b) is a cross-sectional view taken along the line A—A in FIG. 1, showing a state in which there is a space, into which an infusion liquid container is inserted, between a deflated pressurizing bag and a sheet member.

In a state in which the pressurizing bag 11 is not inflated as shown in FIG. 2(b), it has a width slightly larger than that of the sheet member 12, thereby providing a space 13 between the pressurizing bag 11 and the sheet member 12 into which the infusion liquid container 3 can be inserted. As long as the pressurizing bag 11 is inflatable, it may be made of any materials. However, because it exerts large pressure to the infusion liquid container 3 when inflated, it is preferably made of non-stretchable materials. Such materials are preferably plastic sheets reinforced by woven fabrics. A plastic sheet can be heat-sealed in a bag shape to provide a pressurizing bag 11. The sheet member 12 is firmly fixed to the pressurizing bag 11 substantially linearly at both side ends 11a, 11b. The sheet member 12 is preferably constituted by a net, a woven fabric in the form of a mesh having large openings, a transparent plastic film, etc., such that the infusion liquid in the infusion liquid container 3 can be seen from outside.

The volume of the pressurizing bag 11 is determined depending on the volume of the infusion liquid container 3. Because a usual infusion liquid container 3 has a volume of 500 ml, 1000 ml or 300 ml, pressurizing bags 11 having the corresponding sizes are preferably prepared.

The pressurizing bag 11 is provided with an air inlet 11c at a bottom thereof, and an air tube 20 is air-tightly connected to the air inlet 11c. The air tube 20 per se may be constituted by a rubber tube or a plastic tube as long as it has enough flexibility, air tightness and pressure resistance. Mounted to an end of the air tube 20 is an air pump 24 equipped with a pressure-setting means 28 and connected to a power source 26 such as a battery. For miniaturization and reduction in weight, the air pump 24 is preferably of a diaphragm compressor-type.

The air tube 20 is provided with a mechanical safety valve 21 halfway. The mechanical safety valve 21 is provided with a pressure-indicating means for making it possible to confirm the pressure in the system. It is preferable to adjust the pressure in the system by the mechanical safety valve 21, such that the highest blood pressure of the patient is 300 mmHg or less.

The infusion liquid container 3 per se may be one widely used at present. The infusion liquid container 3 has a plug 3a at a bottom thereof, to which the infusion liquid tube 5 is air-tightly connected.

As shown in FIG. 2(a), when the pressurizing bag 11 is inflated with the infusion liquid container 3 disposed in a space 13 between the pressurizing bag 11 and the sheet member 12, the infusion liquid container 3 is substantially uniformly pressed by the pressurizing bag 11 and the sheet member 12. This pressure causes the infusion liquid to flow from the infusion liquid container 3 substantially at a constant flow rate, so that the infusion liquid is injected into the body of the patient via the infusion needle 10 attached to a tip end of the infusion liquid tube 5.

Figure 3:
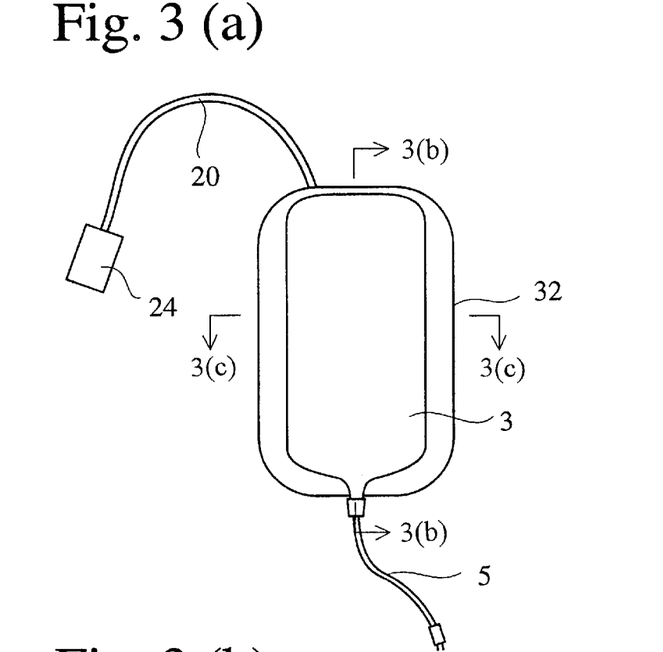
FIG. 3(a) is a schematic, front view partially showing a portable intravenous infusion apparatus according to an embodiment of the present invention.
FIG. 3(b) is a cross-sectional view taken along the line B—B in FIG. 3(a)
FIG. 3(c) is a cross-sectional view taken along the line C—C in FIG. 3(a)

FIGS. 3(a)–3(c) show an inflatable, annular pressurizing bag means 32. The annular pressurizing bag means 32 is constituted by a plurality of air chambers 32a, 32a connected annularly such that they are inflatable inwardly. All air chambers 32a, 32a are air-communicated and one of them is connected to the air tube 20. The infusion liquid container 3 is disposed inside the air chambers 32a, 32a of the annular pressurizing bag means 32, such that the infusion liquid container 3 is pressed equally from all sides when the air chambers 32a, 32a are inflated.

Figure 4:
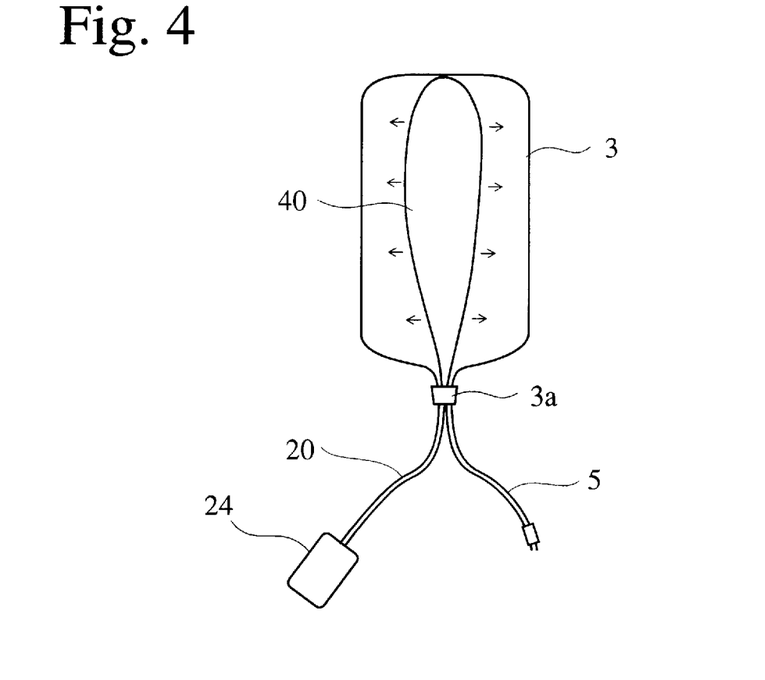
FIG. 4 is a cross-sectional view partially showing a portable intravenous infusion apparatus according to another embodiment of the present invention.
Figure 5:
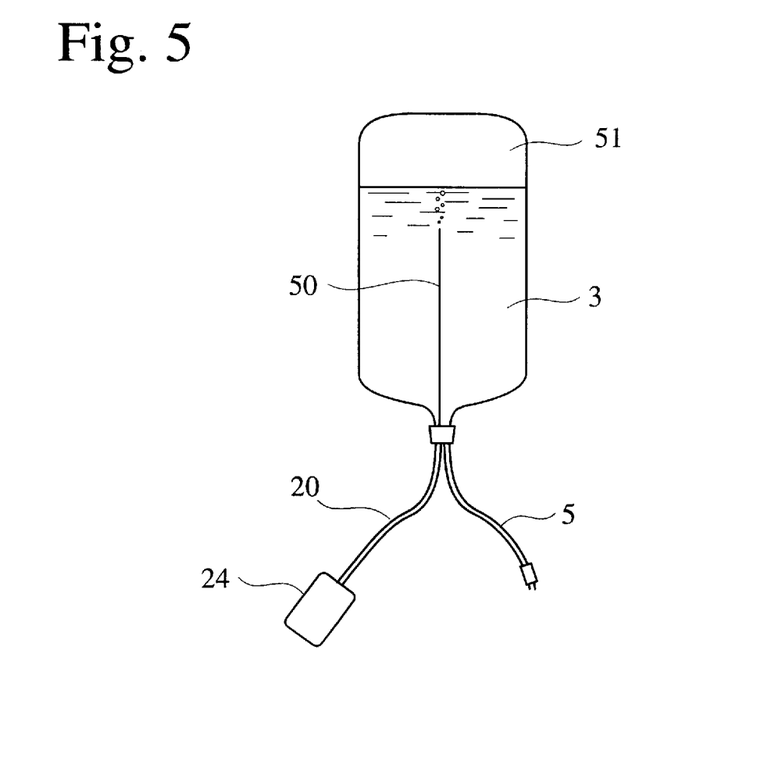
FIG. 5 is a cross-sectional view partially showing a portable intravenous infusion apparatus according to a further embodiment of the present invention.

Instead of the pressurizing bag means 32, a balloon 40 may be disposed in the infusion liquid container 3 such that the inflation of the balloon 40 causes an infusion liquid to flow from the infusion liquid container 3 as shown in FIG. 4. Also, a needle means 50 may be inserted into the infusion liquid container 3 to introduce an air into the infusion liquid container 3, thereby flowing the infusion liquid from the bag 3 as shown in FIG. 5.

Figure 6:
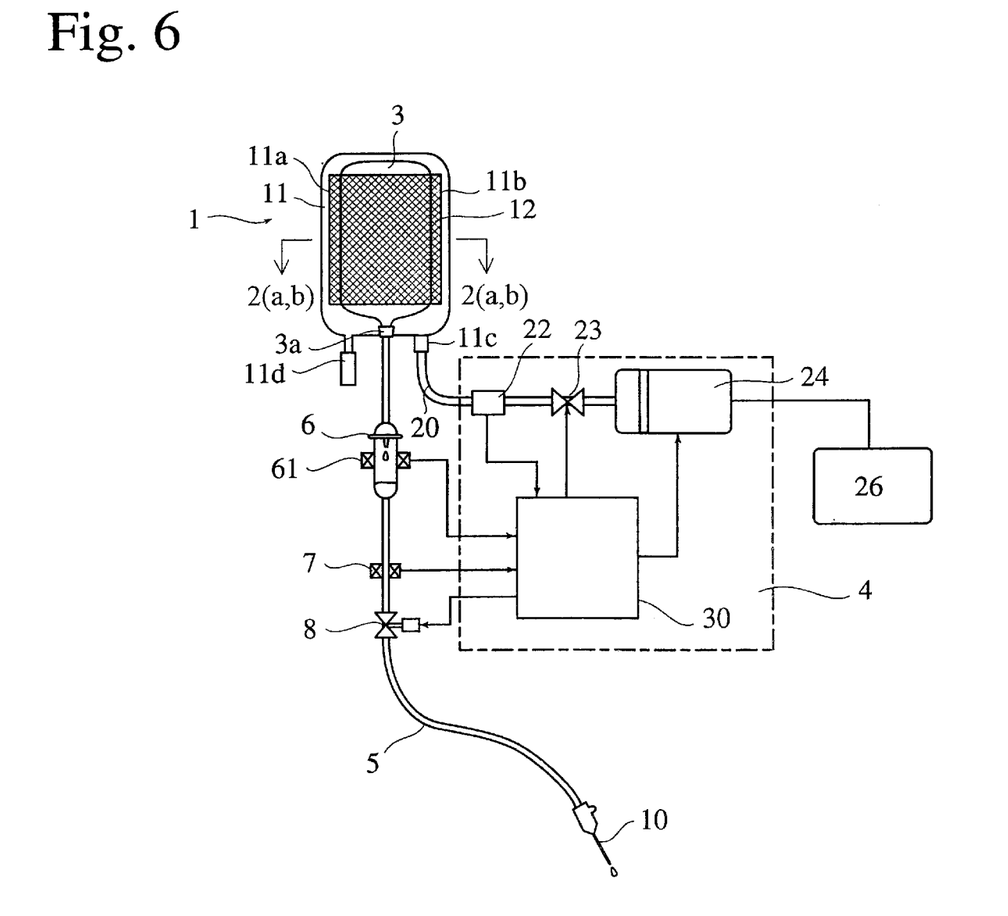
FIG. 6 is a schematic view showing the overall structure of the automatic control-type, portable intravenous infusion apparatus of the present invention.

FIG. 6 shows the overall structure of an automatic control-type, portable installation apparatus according to another preferred embodiment of the present invention. An infusion liquid container 3 has a plug 3a at its bottom, to which an infusion liquid tube S is connected. The infusion liquid tube 5 is provided with a drip-monitoring tube 6 for monitoring the dropping of an infusion liquid, a bubble sensor 7, a clamp device 8 and an infusion needle 10 in this order from above. A drop counter 61 is disposed on both sides of the drip-monitoring tube 6. A pressurizing bag means 1 for holding the infusion liquid container 3 comprises an inflatable pressurizing bag 11 as a pressure-applying means, and a sheet member 12 having side ends each fixed to each of the side ends 11a, 11b of the pressurizing bag 11. Connected to the pressurizing bag 11 is an air tube 20 provided with a pressure sensor 22, a safety valve 23 and an air-supplying means such as an air pump 24. The outputs of the drop counter 61, the bubble sensor 7 and the pressure sensor 22 are supplied to the control means 30, whose output is used to operate the clamp device 8, the safety valve 23 and the air pump 24.

The pressurizing bag 11 is provided with an air inlet 11c at a bottom thereof, and an air tube 20 is air-tightly connected to the air inlet 11c. Mounted to an end of the air tube 20 is an air pump 24 equipped with a motor, as a pressurizing means. The air pump 24 is connected to a power source 26 such as a battery.

The air tube 20 is provided with a safety valve 23 halfway. The safety valve 23 is provided with a pressure-indicating means for making it possible to confirm the pressure in the system. It is preferable to adjust the pressure in the system by the safety valve 23, such that the highest blood pressure of the patient is 300 mmHg or less. The safety valve 23 is connected to a control means 30, such that it is opened depending on the pressure of the pressurizing bag 11 and/or the count number of infusion liquid drops measured by the drop counter 61. Though not shown in FIG. 6, a selector valve may be mounted to the air tube 20 as a backup device for the safety valve 23. The control means 30 may be a commercially available microcomputer.

The infusion liquid tube 5 is equipped with a drip-monitoring tube 6, a bubble sensor 7, a clamp device 8 and an infusion needle 10. The infusion liquid tube 5 may be equipped with an air vent (not shown) to prevent a bubble from entering into the infusion liquid.

The pressurizing bag means 1 comprising a pressurizing bag 11 and a sheet member 12, the air tube 20, the infusion liquid tube 5, the drip-monitoring tube 6 and the air pump 24 may be the same as in FIG. 1.

Figure 7:
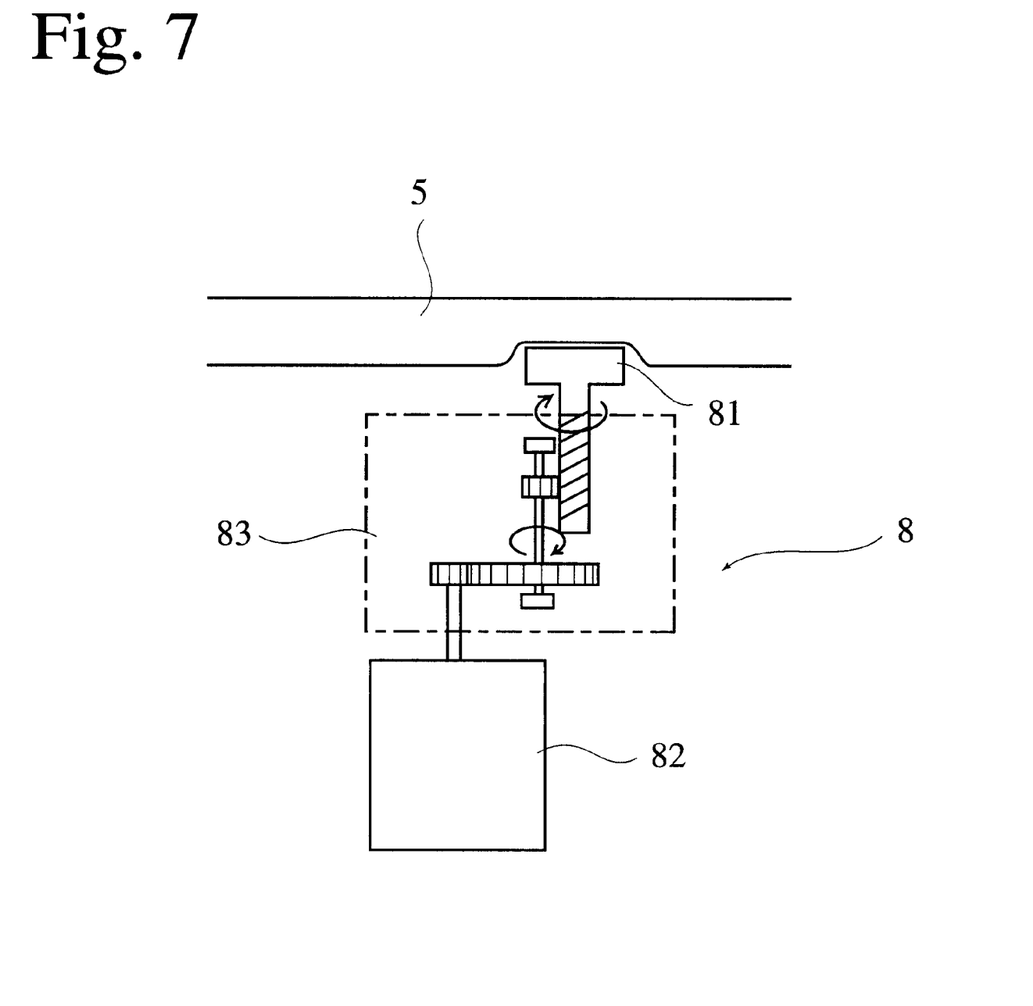
FIG. 7 is a schematic view showing one example of a clamp device used in the automatic control-type, portable intravenous infusion apparatus of the present invention.

FIG. 7 schematically shows one example of the clamp device. The clamp device 8 comprises a clamp means 81 for compressing the infusion liquid tube 5 to control the flow rate of the infusion liquid flowing through the infusion liquid tube 5, a motor 82 for operating the clamp means 81, and a reduction gear means 83. The motor 82 is connected to the control means 30, and the motor 82 rotates in a forward or backward direction depending on an output signal from the control means 30, thereby operating the clamp means 81 such that the infusion liquid tube 5 is compressed or opened.

Incidentally, the clamp device 8 used in the present invention is not restricted to such a compression type, but it may be a rotary type.

The drop counter 61 disposed around the drip-monitoring tube 6 may be an optical sensor comprising, for instance, a light-emitting means such as a light-emitting diode, and a receptor such as a phototransistor, and the light-emitting means and the receptor are disposed such that the infusion liquid drops between them. When the infusion liquid drops, a light from the light-emitting means is shut, which is detected by the receptor. By counting the number of drops shutting the light, the count number N of infusion liquid drops is determined.

The bubble sensor 7 detects whether or not there is a bubble in the infusion liquid flowing through the infusion liquid tube 5. Like the drop counter 61, the bubble sensor 7 per se may be constituted by a light-emitting means and a receptor in such a structure that a bubble passing between them is detected. When the bubble is detected by the bubble sensor 7, a signal of the bubble sensor 7 is supplied to the control means 30, which generates a signal for closing the clamp device 8. In addition, the control means 30 may generate a signal for stopping the air pump 24.

The pressurizing bag 11 may additionally comprise a mechanical safety valve 11d, which has such a structure that it is mechanically opened when the pressure in the pressurizing bag 11 reaches a certain level, for instance, 300 mmHg (corresponding to the highest blood pressure of a patient). The mechanical safety valve 11d may have a structure comprising a valve member biased at a constant pressing power by a spring.

[2] Controlling of Dropping Speed of Infusion Liquid (A) First Embodiment (Control of Pressure in Pressurizing Bag)

Figure 8:
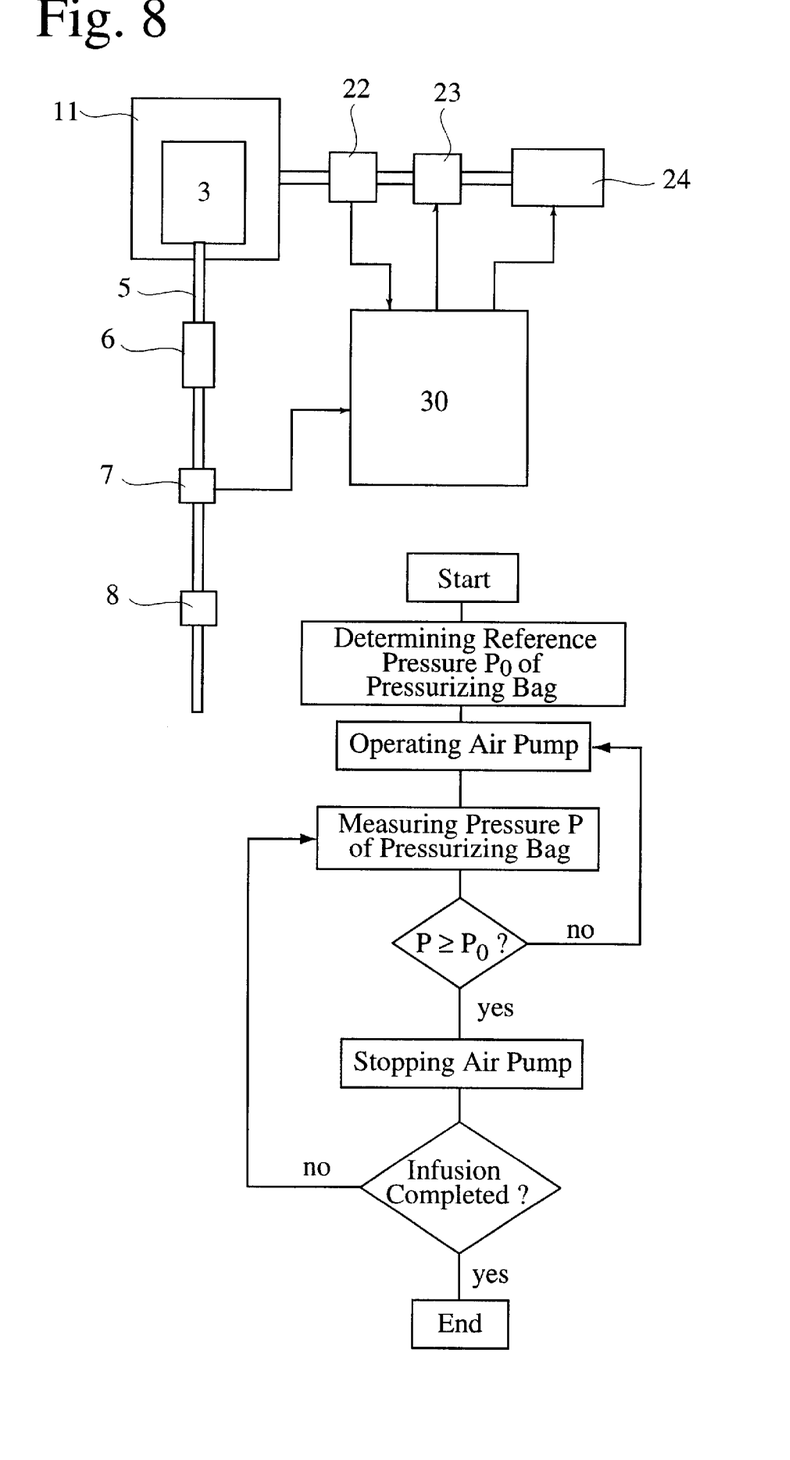
FIG. 8 is a schematic view and a flowchart showing a control system of the first automatic control-type, portable intravenous infusion apparatus according to the present invention.

As shown in FIG. 8, a control system of this embodiment comprises (1) determining the pressure in the pressurizing bag 3 that provides the infusion liquid with a predetermined dropping speed as a reference pressure $P_0$, (2) detecting pressure P in the pressurizing bag 11 by a pressure sensor 22, and supplying its data to a control means 30, and (3) comparing the detected pressure P with the reference pressure $P_0$ by the control means 30. The air pump 24 receives an operation signal when the detected pressure P is lower than the reference pressure $P_0$, or a stop signal when the detected pressure P is higher than the reference pressure $P_0$. Detailed explanation will be made on each of the above steps below.

(1) Determination of Reference Pressure

Pressure (reference pressure $P_0$) in the pressurizing bag 11 necessary for achieving a constant dropping speed generally depends on the sizes and shapes of the pressurizing bag 11 and the infusion liquid container 3, the size and elasticity of the sheet member 12, the amount of an infusion liquid remaining in the infusion liquid container 3, etc. Thus, the pressure obtained from the predetermined dropping speed of the infusion liquid is measured in advance to know the variation of pressure with time, thereby determining the reference pressure $P_0$. Because the reference pressure $P_0$ is applicable to any portable intravenous infusion apparatus of the same type, it is stored in a memory of the control means 30 in each portable intravenous infusion apparatus.

(2) Detection of Pressure in Pressurizing Bag

The pressure P in the pressurizing bag 11 is detected by a pressure sensor 22 mounted to the air tube 20, and the data of the detected pressure P is supplied to the control means 30.

(3) Comparison of pressure P with reference pressure $P_0$

The detected pressure P is compared with the reference pressure $P_0$ by the control means 30. When the detected pressure P is lower than the reference pressure $P_0$, the pressurizing bag 11 does not exert enough pressure to the infusion liquid container 3. Therefore, an operation signal is supplied to the air pump 24, so that the air pump 24 supplies the pressurizing air to the pressurizing bag 3. As a result, the pressurizing bag 11 is inflated, increasing pressure to the infusion liquid container 3. When the detected pressure P exceeds the reference pressure $P_0$, the inflation of the pressurizing bag 11 becomes excessive, resulting in too fast a dropping speed of the infusion liquid. Accordingly, the control means 30 sends a stop signal to the air pump 24 to stop it.

By making the pressure P in the pressurizing bag 11 as close to the reference pressure $P_0$ as possible, the dropping speed of the infusion liquid can be kept substantially constant. For practical application, however, it is difficult to make the pressure P in the pressurizing bag 11 completely equal to the reference pressure $P_0$. Thus, when the difference $\Delta P$ between P and $P_0$ reaches a certain value, a signal for operating or stopping the air pump 24 may be generated. Also, by providing the air tube 20 with the safety valve 23, which is opened in a case where $P-P_0 \geq \Delta P$, the control of the pressure P in the pressurizing bag 11 can be carried out safely and surely.

In the system that the flow rate of the infusion liquid is controlled by adjusting the pressure P in the pressurizing bag 11, control response is generally slow, showing the tendency that the pressure P changes in a relatively wide range. However, experiments have proved that even with a large variation of the pressure P, the flow rate of the infusion liquid can be controlled in a relatively narrow range, causing any problems in practical applications.

(B) Second Embodiment (Control of Pressure in Pressurizing Bag by Count of Drops)

Figure 9:
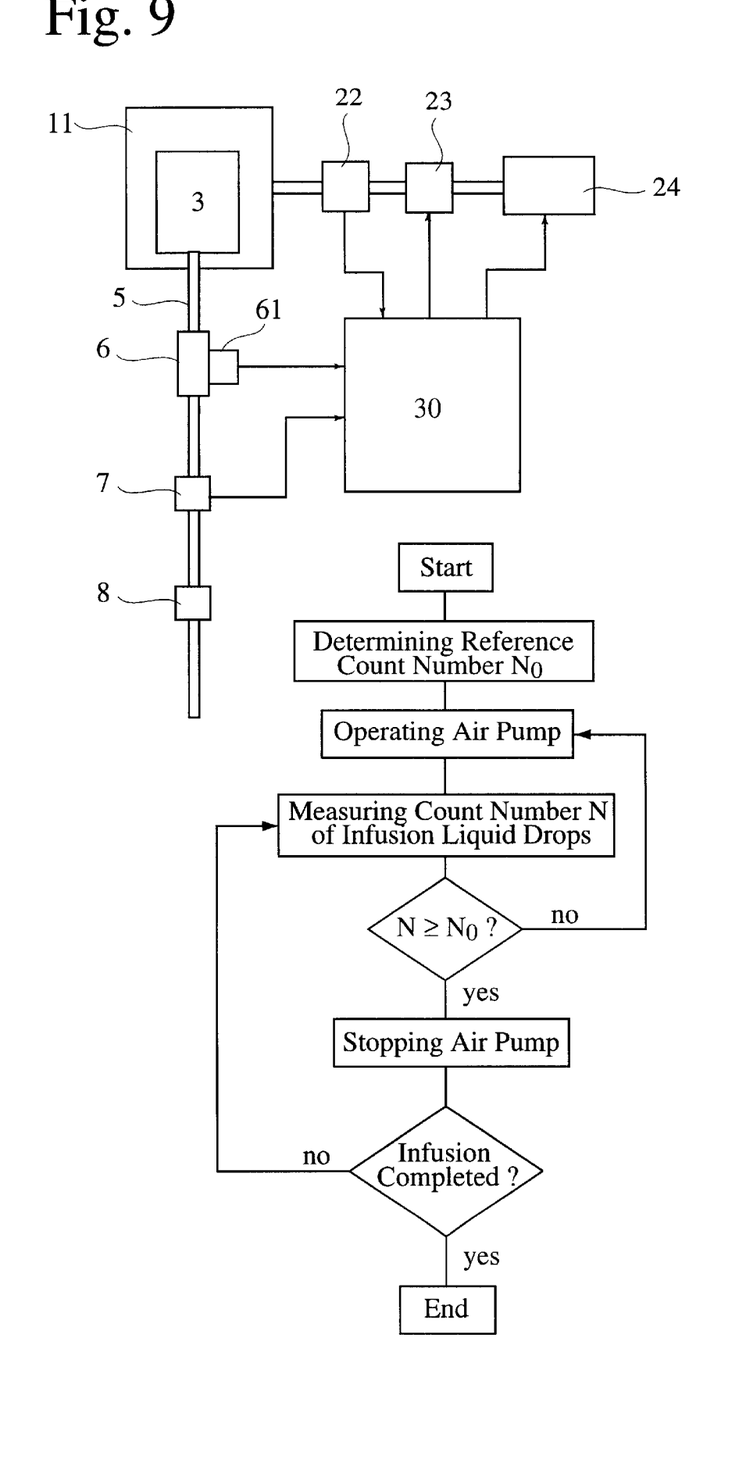
FIG. 9 is a schematic view and a flowchart showing a control system of the second automatic control-type, portable intravenous infusion apparatus according to the present invention.

As shown in FIG. 9, the control system of this embodiment comprises (1) determining in advance the desired count number $N_0$ of infusion liquid drops in a predetermined time period T, which is stored in a memory of the control means 30, (2) counting the number of infusion liquid drops in a predetermined time period T by a drop counter 61 mounted to the drip-monitoring tube 6, and (3) comparing the measured drop count number N with the reference drop count number $N_0$. The air pump 24 is operated when the measured drop count number N is smaller than the reference drop count number $N_0$. Detailed explanation will be made on each of the above steps below.

(1) Determination of Reference Drop Count Number

The desired count number of infusion liquid drops in a predetermined time period T, for instance 30 seconds, is determined in advance, depending on the type of the infusion liquid, the size and the shape of the drip-monitoring tube 6, and the conditions of a patient, etc., and it is stored as a reference drop count number No in a memory of the control means 30.

(2) Measurement of Count Number of Infusion Liquid Drops

The number of drops of the infusion liquid is counted by a drop counter 61 in a predetermined time period T, and it is supplied as a measured drop count number N to the control means 30.

(3) Comparison of Measured Drop Count Number with Reference Drop Count Number

The measured drop count number N supplied to the control means 30 is compared with the reference drop count number $N_0$, and the air pump 24 is operated when the measured drop count number N is smaller than the reference drop count number $N_0$. As pressure to the infusion liquid container 3 increases by inflating the pressurizing bag 11 by the operation of the air pump 24, the amount of the infusion liquid dropped increases, thereby keeping the number of infusion liquid drops substantially constant. For practical applications, however, it is difficult to make the measured drop count number N completely equal to the reference drop count number $N_0$. Thus, when the difference $\Delta N$ between N and $N_0$ reaches a certain value, a signal for operating or stopping the air pump 24 may be generated. Also, by providing the air tube 20 with the safety valve 23, which is opened in a case where $N-N_0 \geq \Delta N$, the control of the pressure P in the pressurizing bag 11 and the drop count number N can be carried out more quickly.

(C) Third Embodiment (Control of Flow Rate of Infusion Liquid Passing Through Clamp Device by Count of Drops)

Figure 10:
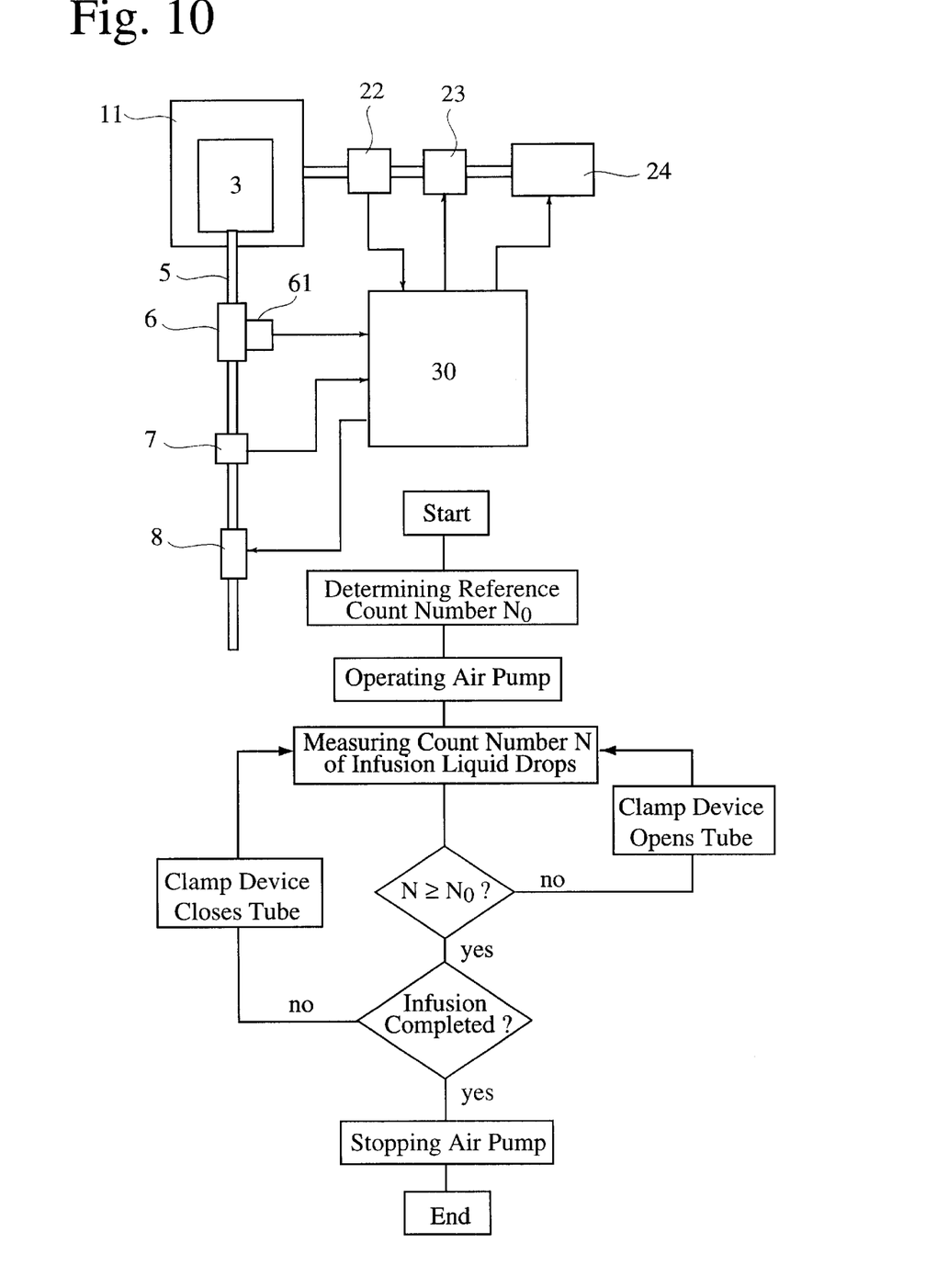
FIG. 10 is a schematic view and a flowchart showing a control system of the third automatic control-type, portable intravenous infusion apparatus according to the present invention.

As shown in FIG. 10, the control system of this embodiment comprises (1) determining in advance the desired count number No of infusion liquid drops in a predetermined time period T, which is stored in a memory of the control means 30, (2) counting the number of infusion liquid drops in a predetermined time period T by a drop counter 61 mounted to the drip-monitoring tube 6, and (3) comparing the measured drop count number N with the reference drop count number $N_0$. The clamp device 8 is operated to increase or decrease the dropping speed of the infusion liquid when the measured drop count number N is larger or smaller than the reference drop count number $N_0$. Detailed explanation will be made on each of the above steps below.

(1) Determination of Reference Drop Count Number and Measurement of Count Number of Infusion Liquid Drops Like the second embodiment, the desired count number No of infusion liquid drops in a predetermined time period T is stored in a memory of the control means 30, and the number N of infusion liquid drops counted by a drop counter 61 in a predetermined time period T is supplied to the control means 30.

(2) Comparison of Measured Drop Count Number with Reference Drop Count Number

The measured drop count number N supplied to the control means 30 is compared with the reference drop count number $N_0$. When the measured drop count number N is larger than the reference drop count number $N_0$, the clamp means 81 of the clamp device 8 projects to press the infusion liquid tube 5, thereby reducing its cross section. Also, when the measured drop count number N is smaller than the reference drop count number $N_0$, the clamp means 81 retreats, thereby permitting the cross section of the infusion liquid tube 5 to return to an original size. Thus, the system that the flow rate of the infusion liquid is controlled by closing or opening the clamp device 8 depending on the measured drop count number N is advantageous in that the flow rate of the infusion liquid is controlled relatively precisely. In this embodiment, too, the air tube 20 may be provided with the safety valve 23, which is opened in a case where $N-N_0 \geq \Delta N$, so that the pressure P in the pressurizing bag 11 and the drop count number N can be controlled more safely and surely.

(D) Other Embodiments

In addition to the above embodiments, the pressure sensor 22, the drop counter 61 and the clamp device 8 may be combined to use the outputs of the pressure sensor 22 and/or the drop counter 61, thereby controlling the air pump 24 and/or the clamp device 8. Also, by utilizing the safety valve 23 mounted to the air tube 20, more varieties of control systems are available. Such specific examples are as follows:

(a) A control system that both of the air pump 24 and the safety valve 23 are controlled by the pressure P detected by the pressure sensor 22.

(b) A control system that both of the clamp device 8 and the safety valve 23 are controlled by the pressure P detected by the pressure sensor 22.

(c) A control system that both of the air pump 24 and the clamp device 8 are controlled by the drop count number N detected by the drop counter 61.

(d) A control system that both of the safety valve 23 and the clamp device 8 are controlled by the drop count number N detected by the drop counter 61.

(e) A control system that all of the air pump 24, the safety valve 23 and the clamp device 8 are controlled by the drop count number N detected by the drop counter 61.

(f) A control system that both of the air pump 24 and the clamp device 8 are controlled by the pressure P detected by the pressure sensor 22 and the drop count number N detected by the drop counter 61.

(g) A control system that all of the air pump 24, the safety valve 23 and the clamp device 8 are controlled by the pressure P detected by the pressure sensor 22 and the drop count number N detected by the drop counter 61.

It should be noted that these control systems are merely examples, and that the present invention is not restricted to them.

[3] Jacket

Figure 14:
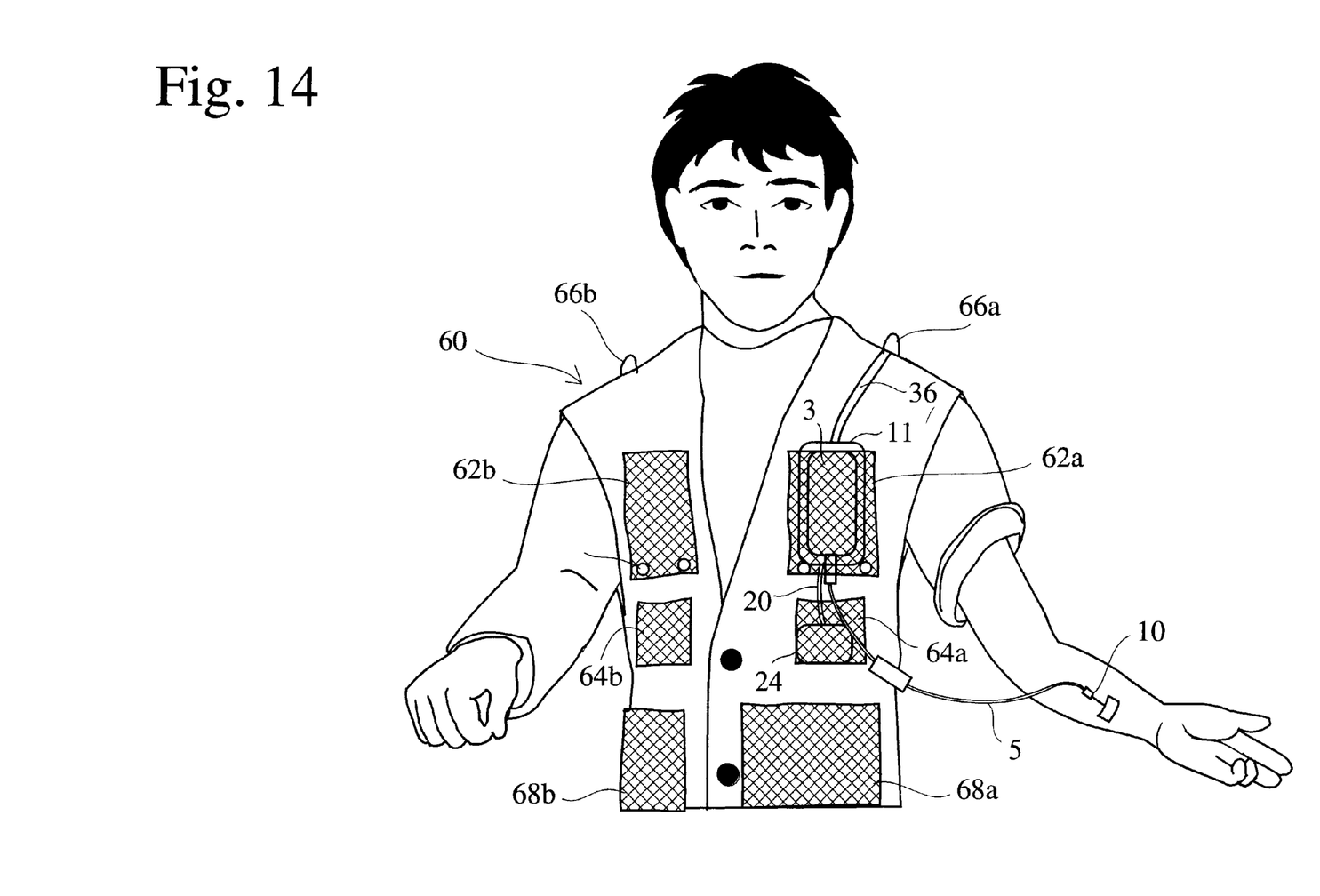
FIG. 14 is a view showing a jacket for carrying the portable intravenous infusion apparatus according to the present invention.

FIG. 14 shows a jacket for holding the portable intravenous infusion apparatus of the present invention. The jacket 60 has a front-open structure comprising a pair of front parts, and each of the front parts has a pocket 62a, 62b for receiving the pressurizing bag 11 and the infusion liquid container 3, a pocket 64a, 64b for receiving the pressure-applying means 24 connected to the pressurizing bag 11, and a horizontally extending pocket 68a, 68b for supporting an arm to which the infusion needle 10 is stuck. Incidentally, the pressurizing bag 11 and the infusion liquid container 3 may be placed in either of the pockets 62a and 62b. The same is true of the pockets 64a, 64b, 68a and 68b. Each of the front parts of the jacket 60 further has a hook 66a, 66b at shoulder for suspending the infusion liquid container 3 via a strap 36.

The present invention will be described in detail below referring to the following examples, without intention of restricting the scope of the present invention defined by the claims attached hereto.

EXAMPLE 1

Control System of Pressure in Pressurizing Bag

Using an automatic control-type, portable intravenous infusion apparatus shown in FIG. 6, the pressure in the pressurizing bag 11 was controlled by the control system shown in FIG. 8. Each member used had the following size:

Pressurizing bag: 500 cm$^3$,

Pressure sensor: Transducer Control Unit TCB-100 (available from Millar),

Infusion liquid set: TS-A450CK (1 cc=15 drops, available from Terumo Corp.), and Infusion liquid: "Haltman S Kobayashi" (50 ml, available from Kobayashi Seiyaku).

Figure 11:
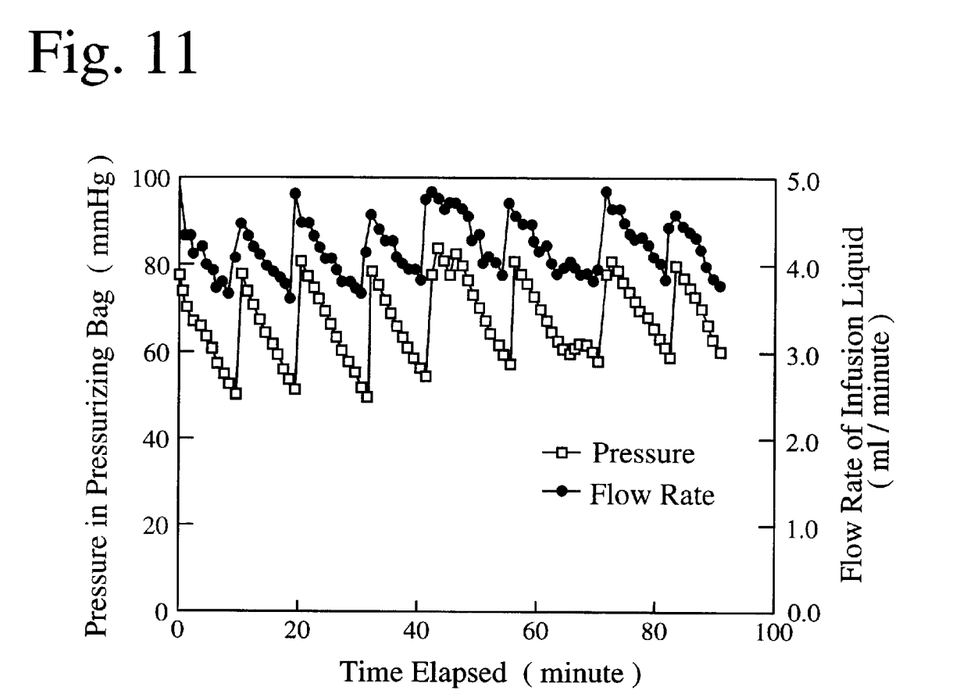
FIG. 11 is a graph showing the change with time of pressure in a pressurizing bag and the flow rate of an infusion liquid according to the pressure control system of the present invention.
Figure 12:
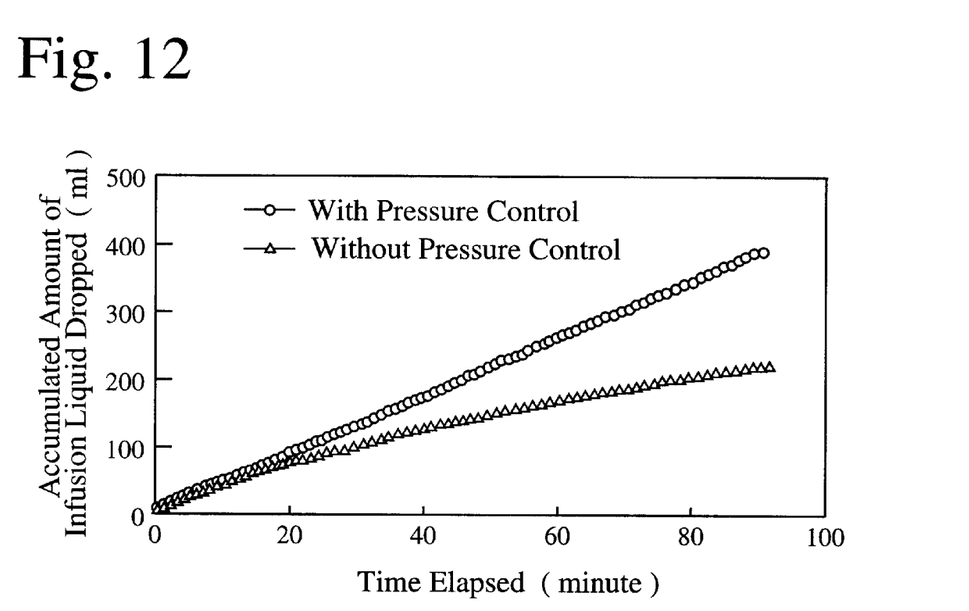
FIG. 12 is a graph showing the accumulated amount of an infusion liquid dropped with or without the pressure control system of the present invention.

With a pressure control range of 50–80 mmHg in the pressurizing bag 11, variations in pressure in the pressurizing bag 11 and flow rate of the infusion liquid were measured. The results are shown in FIG. 11. Also, changes with time of the accumulated amount of an infusion liquid dropped are shown in FIG. 12. FIG. 12 also shows the changes with time of the accumulated amount of an infusion liquid dropped without pressure control.

As is clear from FIG. 11, the amount of an infusion liquid dropped changes depending on the pressure change in the pressurizing bag 11. However, because a change cycle is as short as about 10 minutes, the changes of the dropping speed of the infusion liquid do not cause any problems in a range of the entire infusion time period, for instance 2 hours. Also, as is clear from FIG. 12, the accumulated amount of an infusion liquid dropped linearly increases with time when there is pressure control. But for pressure control, however, the increment of the accumulated amount of an infusion liquid dropped gradually decreases.

Comparative Example 1

Figure 13:
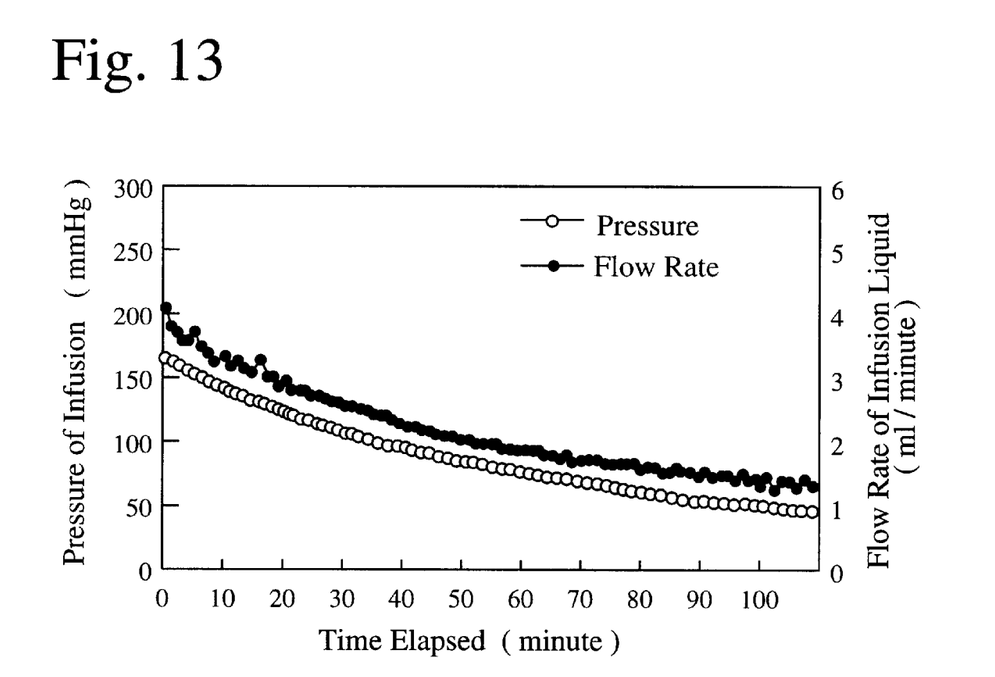
FIG. 13 is a graph showing the change with time of pressure in a pressurizing bag and the flow rate of an infusion liquid when only an initial pressure is applied.

Using the same portable intravenous infusion apparatus as in EXAMPLE 1, an initial pressure in the pressurizing bag 11 was set at 170 mmHg, and measurement was carried out with respect to changes with time of pressure in the pressurizing bag 11 and the amount of an infusion liquid dropped without pressure control. The results are shown in FIG. 13. As is clear from FIG. 13, the dropping speed of the infusion liquid gradually decreases when only the initial pressure is applied.

Though the automatic control-type, portable instillation apparatus of the present invention has been explained referring to the drawings attached hereto, it should be noted that any modifications may be made to the automatic control-type, portable instillation apparatus as long as they do not deviated from the scope of the present invention defined by the claims attached hereto. For instance, the automatic control-type, portable instillation apparatus may have a buzzer and/or a lamp for alarming the irregularity of pressure in the pressurizing bag means.

As described above in detail, in the automatic control-type, portable intravenous infusion apparatus of the present invention, the infusion liquid is dropped at a constant flow rate, and thus the flow rate of the infusion liquid is always controlled substantially constant, by applying a constant pressure to the infusion liquid container instead of causing the infusion liquid to drop from the bag suspended from a hanger by the action of gravity. Therefore, a patient receiving intravenous infusion is freed from inconvenience while leaving the bed. Also, because the infusion liquid container per se may be one conventionally used, only a small cost is newly incurred. Further, because the infusion liquid container can be hung by a hanger when the patient is in the bed, a battery can be shut off, thereby the automatic control-type, portable intravenous infusion apparatus can be used economically.

What is claimed is:

1. A portable intravenous infusion apparatus comprising: an infusion liquid container; an infusion liquid tube communicating with said infusion liquid container, said infusion liquid tube being provided with an air vent means immediately under said infusion liquid container; an infusion needle mounted to a tip end of said infusion liquid tube; and a means for applying a substantially constant pressure to said infusion liquid container, wherein said pressure-applying means comprises (a) a pressurizing bag inflatable by charging air; (b) a sheet member having each side end fixed to each side end of said pressurizing bag, a width of said sheet member being slightly larger than a lateral width of said pressurizing bag in a deflated state; (c) an air tube communicating with said pressurizing bag; (d) an air-supplying means mounted to said air tube; (e) and a safety valve mounted to said air tube, wherein said infusion liquid container is disposed in a space between said pressurizing bag and said sheet member, and wherein said pressurizing bag is inflated by the introduction of air by said air-supplying means, whereby a substantially constant pressure is applied to said infusion liquid container to cause an infusion liquid to flow therefrom.

2. The portable intravenous infusion apparatus according to claim 1, wherein said pressure-applying means comprises (a) an annular pressurizing bag comprising a plurality of air chambers inflatable inwardly by charging air; (b) an air tube communicating with said annular pressurizing bag; and (c) an air-supplying means mounted to said air tube; wherein said infusion liquid container is disposed in a space defined by an inner wall of said annular pressurizing bag, and wherein said pressurizing bag is inflated inwardly by the introduction of air by said air-supplying means, whereby a substantially constant pressure is applied to said infusion liquid container to cause an infusion liquid to flow therefrom.

3. The portable intravenous infusion apparatus according to claim 1, wherein said pressure-applying means comprises (a) an inflatable balloon disposed inside said infusion liquid container; (b) an air tube communicating with said balloon; and (c) an air-supplying means mounted to said air tube; wherein said balloon is inflated by the introduction of air by said air-supplying means, whereby a substantially constant pressure is applied to said infusion liquid container to cause an infusion liquid to flow therefrom.

4. The portable intravenous infusion apparatus according to claim 1, wherein said pressure-applying means comprises (a) an infusion needle disposed inside said infusion liquid container; (b) an air tube communicating with said infusion needle; and (c) an air-supplying means mounted to said air tube; wherein air is introduced into said infusion liquid container through said infusion needle by said air-supplying means, whereby a substantially constant pressure is applied to said infusion liquid container to cause an infusion liquid to flow therefrom.

5. The portable intravenous infusion apparatus according to claim 1, wherein said pressure-applying means comprises an air pump driven by a battery.

6. A jacket for holding the portable intravenous infusion apparatus according to claim 1, having a front-open structure comprising a pair of front parts, each of said front parts having a pocket for receiving said pressurizing bag and said infusion liquid container, a pocket for receiving said pressure-applying means connected to said pressurizing bag, and a horizontally extending pocket for supporting an arm to which said infusion needle is stuck, and each of said front parts further having a shoulder hook for suspending said infusion liquid container.

* * * * *